(12) United States Patent
Greenwald et al.

(10) Patent No.: US 6,214,330 B1
(45) Date of Patent: Apr. 10, 2001

(54) COUMARIN AND RELATED AROMATIC-BASED POLYMERIC PRODRUGS

(75) Inventors: Richard B. Greenwald, Somerset; Yun H. Choe, Piscataway; Annapurna Pendri, Matawan, all of NJ (US)

(73) Assignee: Enzon, Inc., Piscataway, NJ (US)

( * ) Notice: Subject to any disclaimer, the term of this patent is extended or adjusted under 35 U.S.C. 154(b) by 0 days.

(21) Appl. No.: 09/114,860

(22) Filed: Jul. 13, 1998

(51) Int. Cl.⁷ ................................................ A61K 31/74
(52) U.S. Cl. .................... 424/78.01; 549/263; 549/273; 548/400
(58) Field of Search .................. 549/283, 273, 549/263; 424/78.01, 78.02, 78.03, 78.04, 78.05, 78.06, 78.07, 78.08; 548/400, 401, 416

(56) References Cited

U.S. PATENT DOCUMENTS 5,561,119  10/1996  Jacquesy et al. .
5,643,575   7/1997  Martinez et al. .
5,710,135   1/1998  Leenders et al. .

FOREIGN PATENT DOCUMENTS

WO 98/13059  4/1998  (WO) .

OTHER PUBLICATIONS

Wakselman, M. et al An Alkali–labile Substituted Benzyloxycarbonyl Amino–protecting Group, J.C.S. Chem. Comm.; pp. 593–594 (1973).

Carl, P. et al A Novel Connector Linkage Applicable in Prodrug Design, Journal of Medicinal vol. 24, No. 5; (May 1981).

Carpino, L. et al Reductive Lactonization of Strategically Methylated Quinone Propionic Acid Esters and Amides Journal of Organic Chemistry; vol. 54, No. 14; pp. 3303–3310 (1989).

Amsbery, K. et al The Lactonization of 2'–Hydroxyhydrocinnamic Acid Amides: A Potential Prodrug for Amides Journal of Organic Chemistry; vol. 55, No. 23; pp. 5867–5877 (1990).

Amsbery, K. et al Amine Prodrugs Which Utilize Hydroxy Amide Lactonization. II A Potential Esterase–Sensitive Amide Prodrug, Pharmaceutical Research; vol. 8, No. 4; pp. 455–461 (1991).

Jungheim, L. et al Design of Antitumor Prodrugs: Substrates for Antibody Targeted Enzymes, Chemistry Review vol. 94, No 6; pp. 1553–1566 (1994).

Leenders, R. et al B–Glucuronyl Carbamate Based Pro–moieties Designed For Prodrugs In ADEPT, Tetrahedron Letters; vol. 36, No. 10; pp. 1701–1705 (1995).

(List continued on next page.)

Primary Examiner—Dameron L. Jones
(74) Attorney, Agent, or Firm—Roberts & Mercanti, L.L.P.

(57) ABSTRACT

The present invention is directed to double prodrugs containing polymeric-based transport forms. These polymeric prodrugs are preferably of the formula:

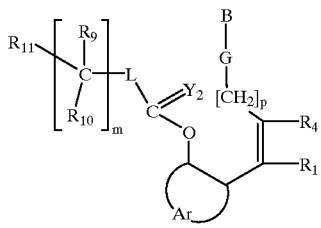

(I)

wherein:

L is

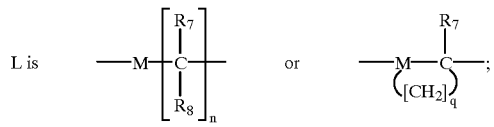

B is H, OH, $OSiR_{13}$, a residue of an amine-containing target moiety or a residue of a hydroxyl-containing target moiety, G is

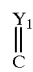

or $CH_2$;

$Y_{1-2}$ are independently O or S;

M is X or Q; where X is an electron withdrawing group and Q is a moiety containing a free electron pair positioned three to six atoms from $C(=Y_2)$;

$R_1$, $R_4$, $R_7$, $R_8$, $R_9$, $R_{10}$ and $R_{13}$ are independently one of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy, except that $R_1$ and $R_4$ can also be a cyano, nitro, carboxyl, acyl, substituted acyl, carboxyalkyl;

Ar is a moiety which when included in Formula (I) forms a multi-substituted aromatic hydrocarbon or a multi-substituted heterocyclic group;

(m) is zero or one;
(n) is zero or a positive integer;
(p) is zero, one or two;
(q) is three or four; and
$R_{11}$ is a substantially non-antigenic polymer.

35 Claims, 3 Drawing Sheets

OTHER PUBLICATIONS

Waldmann, H. et al Synthesis of the Palmitoylated and Farnesylated C–Terminal Lipohexapeptide of the Human N–Ras Protein by Employing an Enzymatically . . . , Angew. Chem. Int.; vol. 34, No. 20; pp. 2259–2262 (1995).

Leenders, R. et al Highly Diastereoselective Synthesis of Anomeric B–O–Glycopyranosyl Carbamates from Isocyanates, Synthesis; pp. 1309–1312; (Nov. 1996).

Wang, B. et al Chemical Feasibility Studies of a Potential Coumarin–Based Prodrug System, Bioorganic & Medicinal Letters; vol. 6, No. 8; pp.945–950 (1996).

Wang, B. et al Coumarin–Based Prodrugs 2. Synthesis and Bioreversibility Studies of an Esterase–Sensitive Cyclic Prodrug of DADLE, and Opiod Peptide, Bioorganic & Medicinal Letters; vol. 6, No. 23; pp. 2823–2826 (1996).

Berry, J. et al 5–Nitrofuran–2–ylmethyl group as a Potential Bioreductively Activated Pro–Drug system, Journal of the Chemical Society, Perkin Trans. 1; (1997).

Shan, D. et al Prodrug Strategies Based on Intramolecular Cyclization Reactions, Journal of Pharmaceutical Sciences; vol. 86, No. 7; (Jul. 1997).

Wang, B. et al Synthesis of a Novel Esterase–Sensitive Cyclic Prodrug System for Peptides that Utilizes a "Trimethyl Lock"—Facilitated Lactonization Reaction, J. of Org. Chem.; vol. 62, No. 5; pp. 1363–1367 (1997).

Wang, B. et al A Photo–Sensitive Protecting Group for Amines Based on Coumarin Chemistry, Chem. Pharm. Bull.; vol. 45 No. 4; pp. 715–718 (1997).

Wang, B. et al Coumarin–Based Prodrugs. Part 3. Structural Effects on the Release Kinetics of Esterase-sensitive Prodrugs of Amines, Bioorganic & Medicinal Chemistry; vol. 6; pp. 417–426; (1998).

Bundgaard, H. The Double Prodrug Concept and its Applications, Advanced Drug Delivery Reviews; vol. 3; pp. 39–65; (1989).

Method A.

Method B.

COUMARIN AND RELATED AROMATIC-BASED POLYMERIC PRODRUGS

TECHNICAL FIELD

The present invention relates to double prodrugs. In particular, the invention relates to polymeric-based double prodrugs having reversible linkages involving amino or hydroxyl moieties of chemical compounds and biologically active materials such as enzymes, proteins and the like.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal agent is either insoluble in aqueous fluids or is rapidly degraded in vivo. For example, alkaloids are often especially difficult to solubilize.

One way to solubilize medicinal agents is to include them as part of a soluble prodrug. Prodrugs include chemical derivatives of a biologically-active parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols. See *Remington's Pharmaceutical Sciences*, 16th Ed., A. Osol, Ed. (1980), the disclosure of which is incorporated by reference herein.

Prodrugs are often biologically inert or substantially inactive forms of the parent or active compound. The rate of release of the active drug, i.e. the rate of hydrolysis, is influenced by several factors but especially by the type of bond joining the parent drug to the modifier. Care must be taken to avoid preparing prodrugs which are eliminated through the kidney or reticular endothelial system, etc. before a sufficient amount of hydrolysis of the parent compound occurs. By incorporating a polymer as part of the prodrug system, one can increase the circulating half-life of the drug.

Although the above-mentioned concept of prodrug-based delivery systems has proven to be useful in many instances, there are nonetheless situations where alternatives are desired. For example, Bundgaard in "The Double Prodrug Concept and Its Applications" in *Advanced Drug Delivery Reviews*, 3 (1989) 39–65, (the contents of which are hereby incorporated by reference) pointed out that in many cases it is difficult to obtain a prodrug which has the proper combination of adequate stability in vitro and high susceptibility to regenerate the parent drug in vivo. As pointed out by Bundgaard, a promising means of overcoming some of the previously encountered shortcomings involves the use of cascade latentiation or "pro-prodrugs". In such systems, the hydrolytic reaction sequence involves a first step which usually is an enzymatic cleavage and the second involves a non-enzymatic hydrolysis that occurs only after the first has taken place. The use of polymeric-based transport systems as part of cascade latentiation technology was not disclosed.

The problems associated with preparing prodrugs of amine-containing drugs was recently highlighted by Shan, D. et al. in "Prodrug Strategies Based on Intramolecular Cyclization Reactions" *J. Pharm. Sci.* July 1997 Vol.86, No.7, 765–767, (the contents of which are hereby incorporated by reference). To avoid the relative stability of the amide bond, the authors disclose prodrugs which incorporate various moieties which are capable of undergoing intramoleuclar cyclization reactions to release the parent drug. The chemical or biological triggering mechanisms which initiate the cyclization reactions are independent of those which are required for releasing the original drug via hydrolysis of the amide bond. A non-polymeric-containing coumarin-based system is among those disclosed.

Another non-polymeric coumarin-based system is disclosed by Wang, B. et al. in "Chemical Feasibility Studies of a Potential Coumarin-Based Prodrug System" in *Bioorganic & Medicinal Chemistry Letters*, Vol.6, No.8, pp 945–950, 1996. After esterase catalyzed hydrolysis of the phenolic ester, lactonization and release of the parent compounds was rapid, with $t_{1/2}$ being 1.5 to 31 minutes. The technique was also used by the authors to prepare a prodrug of the opioid peptide DADLE. See *Bioorganic & Medicinal Chemistry Letters*, Vol.6, No.23, pp 2823–2826, 1996. The contents of each of the foregoing are hereby incorporated by reference.

It is believed that in spite of the reported work in the field of double prodrugs, some specific problems were not addressed sufficiently. For example, the previously reported techniques do not sufficiently address the solubility problems of many amine-containing parent compounds. In addition, the problem of designing in variable increases in circulating half-life for the prodrug prior to cyclization and release of the parent compound has also not been addressed. Thus, there continues to be a need to provide additional technologies for forming prodrugs which would benefit from the double prodrug concept. For example, it would be advantageous to provide the artisan with alternative techniques for transport carrier attachment so as to regulate biological effect. Furthermore, it would be desirable to provide additional techniques to address problems associated with involving amino residues and/or hydroxyl residues of parent compounds and thus avoid excessively fast or slow hydrolysis prodrug of the transport form from the parent compound at physiological pH.

SUMMARY OF THE INVENTION

The present invention addresses the shortcomings described above. In one aspect of the invention, compounds of Formula (I) are provided:

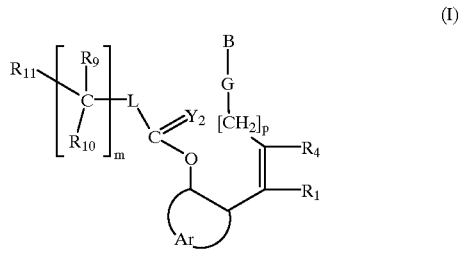

(I)

wherein:

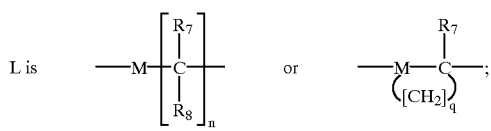

B is H, OH, $OSiR_{13}$, a residue of an amine-containing target moiety or a residue of a hydroxyl-containing moiety;

G is

or $CH_2$;

$Y_{1-2}$ are independently O or S;

M is X or Q; where
X is an electron withdrawing group; and
Q is a moiety containing a free electron pair positioned three to six atoms from $C(=Y_2)$;

$R_1$, $R_4$, $R_7$, $R_8$, $R_9$, $R_{10}$ and $R_{13}$ are independently one of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy, except that $R_1$ and $R_4$ can also be a cyano, nitro, carboxyl, acyl, substituted acyl, carboxyalkyl;

Ar is a moiety which when included in Formula (I) forms a multi-substituted aromatic hydrocarbon or a multi-substituted heterocyclic group;

(m) is zero or one;
(n) is zero or a positive integer;
(p) is zero or one;
(q) is three or four; and
$R_{11}$ is a polymer residue such as a water-soluble polyalkylene oxide.

In certain preferred aspects, B is a leaving group such as N-hydroxybenzotriazolyl, N-hydroxyphthalimidyl, halogen, p-nitrophenoxy, imidazolyl, N-hydroxysuccinimidyl, thiazolidinyl thione, or other activating groups. Alternatively, B is a residue of any amino-containing or hydroxyl-containing compound for which one or more of improved aqueous solubility, decreased antigenicity, prodrug and/or controlled release delivery is desired. For example, B, can be a residue of an enzyme, protein, or organic compound such as daunorubicin, doxorubicin,p-aminoaniline mustard, camptothecin, paclitaxel, Ara C, etc.

For purposes of the present invention, the term "residue" shall be understood to mean that portion of a biologically active compound which remains after it has undergone a substitution reaction in which the prodrug carrier portion has been attached.

For purposes of the present invention, the term "alkyl" shall be understood to include straight, branched, substituted $C_{1-2}$ alkyls, including alkoxy, $C_{3-8}$ cycloalkyls or substituted cycloalkyls, etc.

The double prodrugs of the present invention are thus unique delivery systems. Preferably, the polymeric portion is first released by hydrolysis or esterase activity and then the resultant "second prodrug" moiety undergoes a lactonization reaction to regenerate the amine-containing bioactive compound in vivo.

Some of the chief advantages of the double prodrug compounds of the present invention are that they are capable of solubilizing amine- or hydroxyl-containing compounds and extending their half-lives as compared to the native or even "second" prodrug counterparts. The polymeric portion can also impart an antigenicity-reducing effect on the parent compound. Another advantage of the systems of the present invention is that the linkage between the polymer portion and the "second prodrug" compound as described above, is designed to hydrolyze or otherwise cleave at a rate which allows the compound to retain its enhanced solubility and circulating half-life. The native drug, however, is still not released at this point. Only after the "second prodrug" undergoes the relatively rapid lactonization reaction, will the desired native or parent molecule be released. It is readily apparent that this double prodrug approach of the present invention offers unique and unexpected characteristics which enhance the circulating half-life and solubility of native or unmodified molecules.

Methods of making and using the compounds and conjugates described herein are also provided.

DETAILED DESCRIPTION OF THE INVENTION

A. Formula (I)

Figure 1:
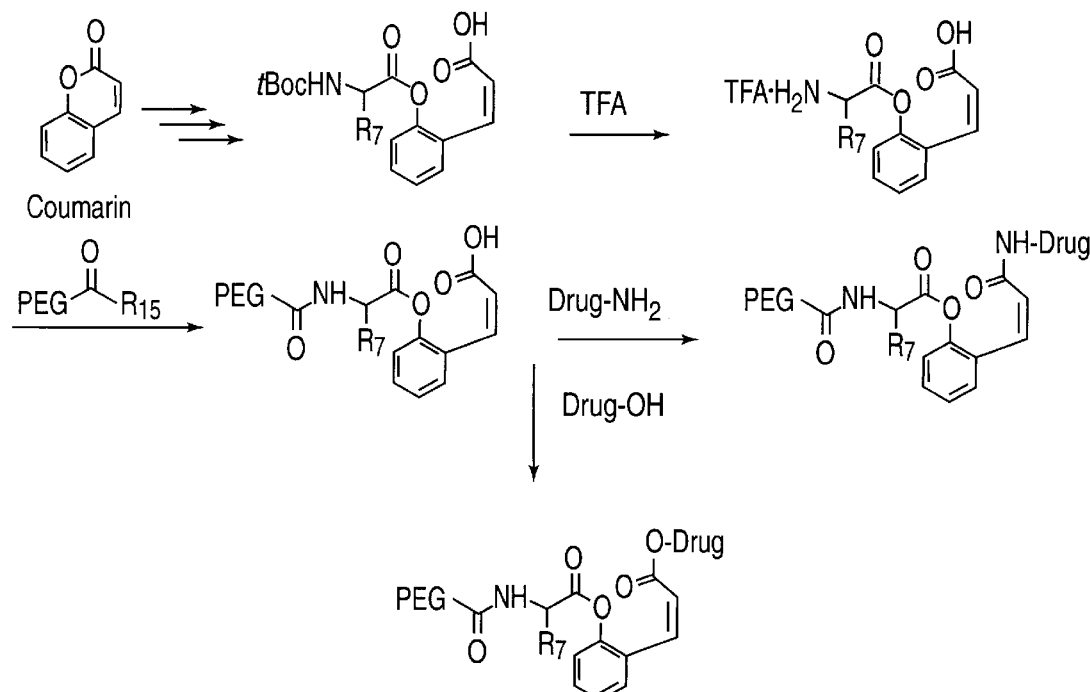
FIG. 1–4 schematically illustrate methods of preparing double prodrugs of the present invention.

In one aspect of the invention, there are provided compounds of formula (I):

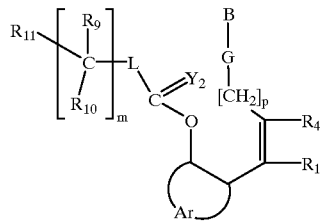

wherein:

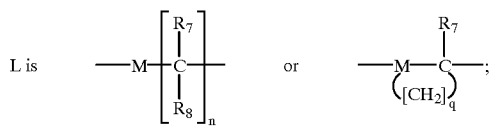

B is H, OH, $OSiR_{13}$, a residue of an amine-containing target moiety or a residue of a hydroxyl-containing moiety;

G is

or $CH_2$;

$Y_{1-2}$ are independently O or S;

M is X or Q; where
  X is an electron withdrawing group;
  Q is a moiety containing a free electron pair positioned three to six atoms from C(=$Y_2$);
  $R_1$, $R_4$, $R_7$, $R_8$, $R_9$, $R_{10}$ and $R_{13}$ are independently one of hydrogen, $C_{1-6}$ alkyls, $C_{3-12}$ branched alkyls, $C_{3-8}$ cycloalkyls, $C_{1-6}$ substituted alkyls $C_{3-8}$ substituted cycloalkyls, aryls, substituted aryls, aralkyls, $C_{1-6}$ heteroalkyls, substituted $C_{1-6}$heteroalkyls, $C_{1-6}$ alkoxy, phenoxy, $C_{1-6}$ heteroalkoxy, except that $R_1$ and $R_4$ can also be a cyano, nitro, carboxyl, acyl, substituted acyl, carboxyalkyl;
Ar is a moiety which when included in Formula (I) forms a multi-substituted aromatic hydrocarbon or a multi-substituted heterocyclic group;
  (m) is zero or one;
  (n) is zero or a positive integer;
  (p) is zero or one;
  (q) is three or four; and
  $R_{11}$ is a polymer residue.
$Y_{1-2}$ are preferably O, and (p) is preferably one. In additional preferred embodiments $R_1$ and $R_4$ are independently hydrogen, $CH_3$, or $CH_2CH_3$. For purposes of the present invention, substituted alkyls include carboxyalkyls, aminoalkyls, dialkylaminoalkyls, hydroxyalkyls and mercaptoalkyls; substituted cycloalkyls include moieties such as 4-chlorocyclohexyl; aryls include moieties such as napthyl; substituted aryls include moieties such as 3-bromophenyl; aralkyls include moieties such as toluyl; heteroalkyls include moieties such as ethylthiophene; substituted heteroalkyls include moieties such as 3-methoxythiophene; alkoxy includes moieties such as methoxy; and phenoxy includes moieties such as 3-nitrophenoxy. Halo- shall be understood to include fluoro, chloro, iodo and bromo.

B. Preferred Aspects of Aromatic Portion of Formula (I)

For purposes of the present invention, Ar represents a moiety which results in the formation of a multi-substituted aromatic hydrocarbon or a multi- substituted heterocyclic group in Formula (I). A key feature, however, is that the moiety is aromatic in nature. Generally, to be aromatic, π electrons must be shared within a "cloud" both above and below the plane of a cyclic molecule. Furthermore, the number of π electrons must satisfy the Hückel rule (4n+2). Those of ordinary skill in the art will realize that a myriad of moieties will satisfy the aromatic requirement of Ar in Formula (I) and thus will be suitable for use herein.

Preferred aromatic moieties of the present invention include, without limitation:

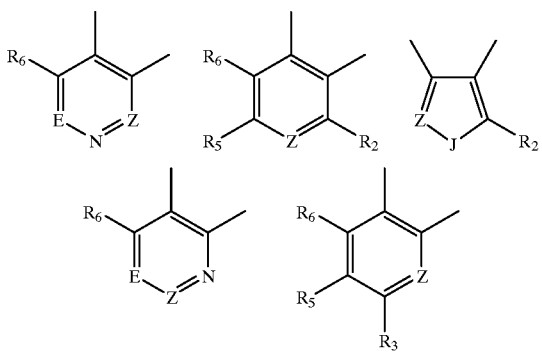

wherein J is O, S, or $NR_1$, E and Z are independently $CR_2$ or $NR_1$; and $R_2$, $R_3$, $R_5$ and $R_6$ are independently selected from the group consisting of hydrogen, $C_{1-6}$ alkyls, $C_{1-6}$ alkoxy, phenoxy, $C_{1-8}$ heteroalkyls, $C_{1-8}$ heteroalkoxy, substituted $C_{1-6}$ alkyls, $C_{3-8}$ cycloalkyls, $C_{3-8}$ substituted cycloalkyls, aralkyls, aryls, substituted aryls, such as aryls substituted with halo-, nitro- and cyano-; carboxy-, carboxyalkyl, alkylcarbonyl, etc. In preferred aspects of the present invention, $R_2$, $R_3$, $R_5$ and R6 are either hydrogen or a lower, i.e. $C_{1-6}$ alkyl or substituted alkyl. More preferably, $R_2$, $R_3$, $R_5$ and $R_6$ are hydrogen. Isomers of the five and six-membered rings are also contemplated as well as benzo- and dibenzo- systems such as anthracine, napthlene and their related congeners are also contemplated. Particularly preferred moieties are based on coumarin and coumarin derivatives.

C. The Double Prodrug Linkage Portion

The double prodrug linkages of the transport systems of the present invention are selected to hydrolyze via an esterase catalyzed hydrolysis in vivo at a rate which generates sufficient amounts of the "second" prodrug compound within a suitable time after administration. The term "sufficient amounts" for purposes of the present invention shall mean an amount which later undergoes sufficient lactonization in vivo to release the parent compound and achieve a desired effect. In other aspects of this linking/spacer moiety, (n) is preferably an integer from about 1 to about 12 and more preferably 1 or 2; and $R_{7-10}$ are preferably hydrogen or a lower alkyl, when present.

1. The Electron Withdrawing Group X

Within the formula (I) described above, M may be X which is designated as an electron withdrawing group. In particular, X can be selected from moieties such as O, $NR_{12}$,

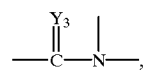

S, SO and $SO_2$ where $Y_3$ is the same as that defined for $Y_1$ and $R_{12}$ is the same as that defined for $R_1$, i.e. H, $C_{1-6}$ alkyls, branched alkyls, aryls, substituted aryls, $C_{1-6}$ alkyl aralkyls, heteroalkyls, substituted heteroalkyls or substituted $C_{1-6}$ alkyls such as carboxyalkyls, aminoalkyls, dialkylaminoalkyl, hydroxyalkyls or mercaptoalkyls, to name but a few. Preferably, X is O, $NR_{12}$ or

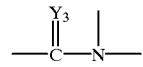

and $R_{12}$ is H.

2. Q Portion of the Linker

When M is Q, the polymer, $R_{11}$, is preferably attached to Q via a heteroatom such as oxygen. Q is a moiety containing a free electron pair positioned three to six atoms from the C(=$Y_2$) moiety. In a preferred embodiment, the free electron pair is five atoms from this oxygen. Q can be selected from the non-limiting list of $C_{2-4}$ alkyls or $C_{3-8}$ cycloalkyls, aryls or aralkyl groups substituted with a member of the group consisting of O, S and $NR_{12}$, wherein $R_{12}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$heteroalkyls. The free electron pair can be anywhere along the Q moiety as long as the defined spacing between the free electron pair and the oxygen is maintained.

In these embodiments, $R_{11}$ is attached to Q via $NR_{12}$, O, or S. Thus, Q assists hydrolysis of the prodrug linkage by anchimeric assistance because the free electron pair moiety can generate a three- to six-membered, but preferably five-membered, ring by-product upon hydrolysis of the preferably ester linkage.

Q can also be selected from the group consisting of $C_{2-4}$ alkyls, cycloalkyls, aryls, aralkyl groups substituted with a member of the group consisting of NH, O, S, —$CH_2$—C(=O)—NH—, and ortho-substituted phenyls such as

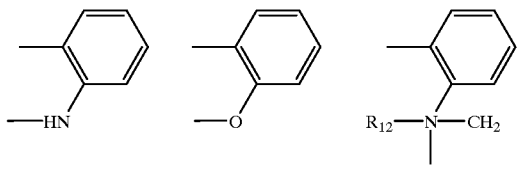

3. Drug or Parent Moiety Generation Via Hydrolysis of the Prodrug

The prodrug compounds of the present invention are designed so that the rate of hydrolysis>the rate of elimination in plasma.

The linkages included in the compounds have hydrolysis rates in the plasma of the mammal being treated which is fast enough to allow sufficient amounts of the parent compounds, i.e. the amino-containing bioactive compound, to be released prior to elimination. Some preferred compounds of the present invention, i.e. those in which (n) is 1 or 2, have a $T_{1/2}$ for hydrolysis in plasma ranging from about 5 minutes to about 12 hours. Preferably, the compositions have a plasma $T_{1/2}$ hydrolysis ranging from about 0.5 to about 8 hours and most preferably from about 1 to about 6 hours.

4. Coumarin and Coumarin-like Facilitated Lactonization and Native Drug Regeneration Once the first ester hydrolysis of the double prodrug has taken place, usually via esterase activity or pH-moderated activity or cyclization reaction, the polymeric residue is cleaved and the resultant second prodrug moiety remains. This single prodrug entity will undergo a further independent lactonization reaction in vivo to produce the desired native or parent compound. This spontaneous reaction occurs after the hydrolysis of the polymeric portion occurs and is initiated by simple proton removal of the phenolic intermediate which causes the following lactonization which then releases the amine-containing parent compound. A representative reaction is shown below.

D. Substantially Non-Antigenic Polymers

The "double prodrug" compositions of the present invention include a polymeric residue, $R_{11}$ which is described in detail below.

In preferred aspects of the invention, $R_{11}$ includes a capping group A which can be hydrogen, $C_{1-6}$ alkyl moieties, carboxyalkyl, dialkyl acyl urea alkyls, or a compound of formula (II) shown below which forms a bis-system:

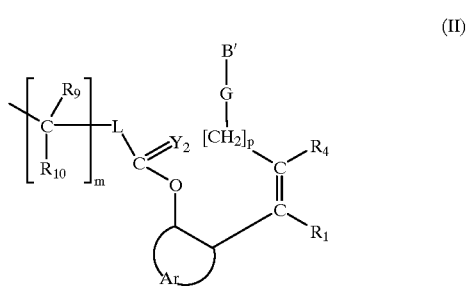

(II)

wherein B' is the same as B or another member of the group defined by B and the remaining variables are as set forth above with regard to Formula (I).

Suitable examples of such polymers include polyalkylene oxides such as polyethylene glycols which are also preferably substantially non-antigenic. The general formula for PEG and its derivatives, i.e. A'—O—$(CH_2CH_2O)_x$—$(CH_2)_n$—A, where (x) represents the degree of polymerization (i.e. 10–2,300) or number of repeating units in the polymer chain and is dependent on the molecular weight of the polymer, (n) is zero or a positive integer, (A) is a capping group as defined herein, i.e. an —H, amino, carboxy, halo, $C_{1-6}$ alkyl or other activating group and A' is the same as A or another A moiety. Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998"; the disclosure of each is incorporated herein by reference. It will be understood that the water-soluble polymer will be functionalized for attachment to the linkage via M, X or Q herein. As an example, the PEG portion of the prodrugs can be the following non-limiting compounds: —C(=Y)—$(CH_2)_n$—O—$(CH_2CH_2O)_x$—A, —C(=Y)—Y—$(CH_2)_n$—

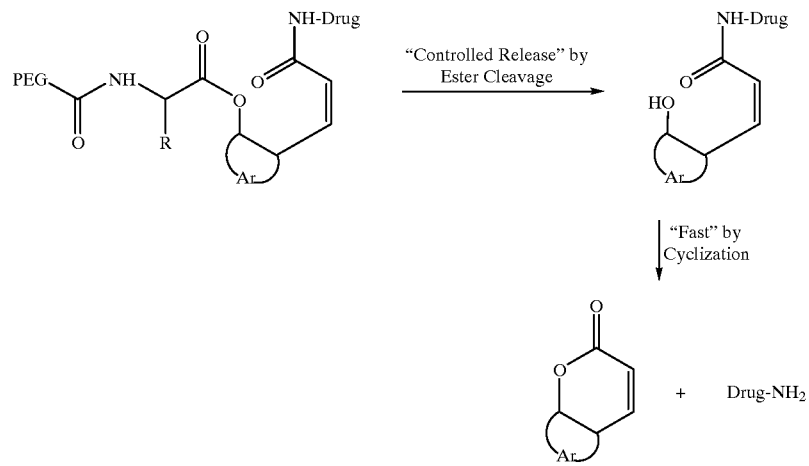

O—(CH₂CH₂O)$_x$—A and —C(=Y)—NR$_{12}$—(CH$_2$)$_n$—O—(CH₂CH₂O)$_x$—A, where Y is O or S and R$_{12}$, (n) and (x) are as defined above.

In particular, polyethylene glycols (PEG's), mono-activated, C$_{1-4}$ alkyl-terminated PAO's such as mono-methyl-terminated polyethylene glycols (mPEG's) are preferred when mono- substituted polymers are desired; bis-activated polyethylene oxides are preferred when disubstituted prodrugs are desired.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting mPEG-OH to an ethyl ester followed by saponification. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in molecular weight, polymers ranging from about 2,000 to about 100,000 are usually selected for the purposes of the present invention. Molecular weights of from about 5,000 to about 50,000 are preferred and 5,000 to about 40,000 are particularly preferred. The molecular weight of the polymer selected for inclusion in the "double prodrug" must be sufficient so as to provide sufficient circulation of the "double prodrug" before hydrolysis of the linker. Within the ranges provided above, polymers having molecular weight ranges of at least 20,000 are preferred for chemotherapeutic and organic moieties. In the case of nucleophiles such as some proteins, enzymes and the like, polymers having a molecular weight range of from about 2,000 to about 20,000 are preferred.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immune response in mammals.

E. The Polymeric Double Prodrug Transport System

The double prodrugs of the present invention can be prepared in at least two fashions. One technique schematically shown in FIG. 1, which uses coumarin as an illustrative starting Ar moiety material, includes a. providing an intermediate compound (III)

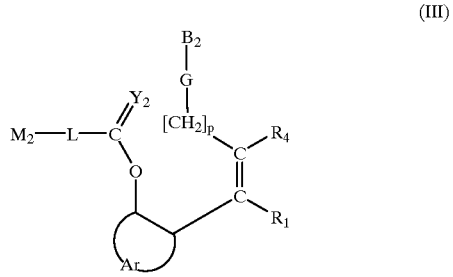

(III)

where M$_2$ is a cleavable or reversible protecting group; B$_2$ is a leaving group such as OH; and all other variables are as set forth above with regard to Formula (I);

b. treating the intermediate compound (III) with a strong acid such as TFA (trifluoroacetic acid) or other trihaloacetic acid, HCl, sulfuric acid, etc., or catalytic hydrogenation to remove the protecting group; and c. reacting the unprotected intermediate compound (III) with a moiety capable of reacting with M, such as an activated polymer, i.e. a polymer having a reactive functional group, (designated "R$_{15}$" in FIG. 1) e.g., p-nitrophenyl or succinimidyl carbonate, carbonyl imidazole, thiazolidine thione or the like, and optionally present spacer e.g. R$_{11}$—[CR$_9$R$_{10}$]$_m$ to form an activated double prodrug transport form of formula (IV):

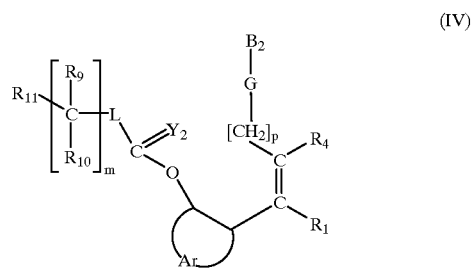

(IV)

where all other variables are as set forth above with regard to Formula (I); and optionally d. attaching the parent amine-containing or hydroxyl-containing compound residue to compound (IV) by displacing B$_2$ in a reaction with an amine-containing or hydroxyl-containing compound such as a drug-NH$_2$ or drug-OH as shown in FIG. 1.

Figure 2:
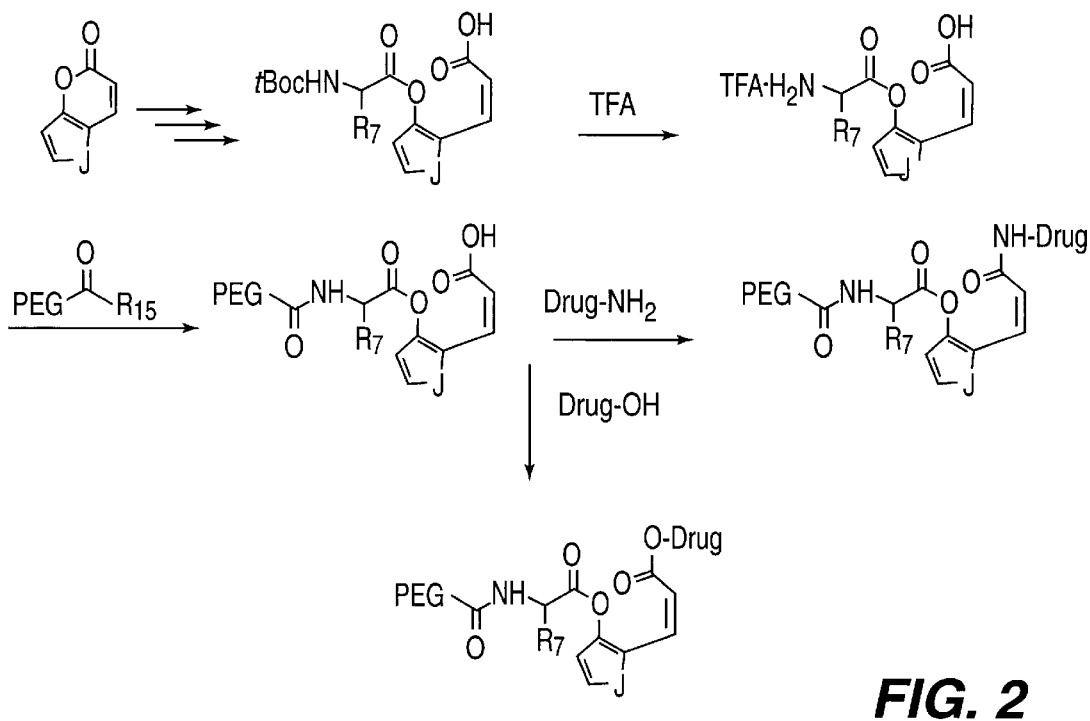
Figure 3:
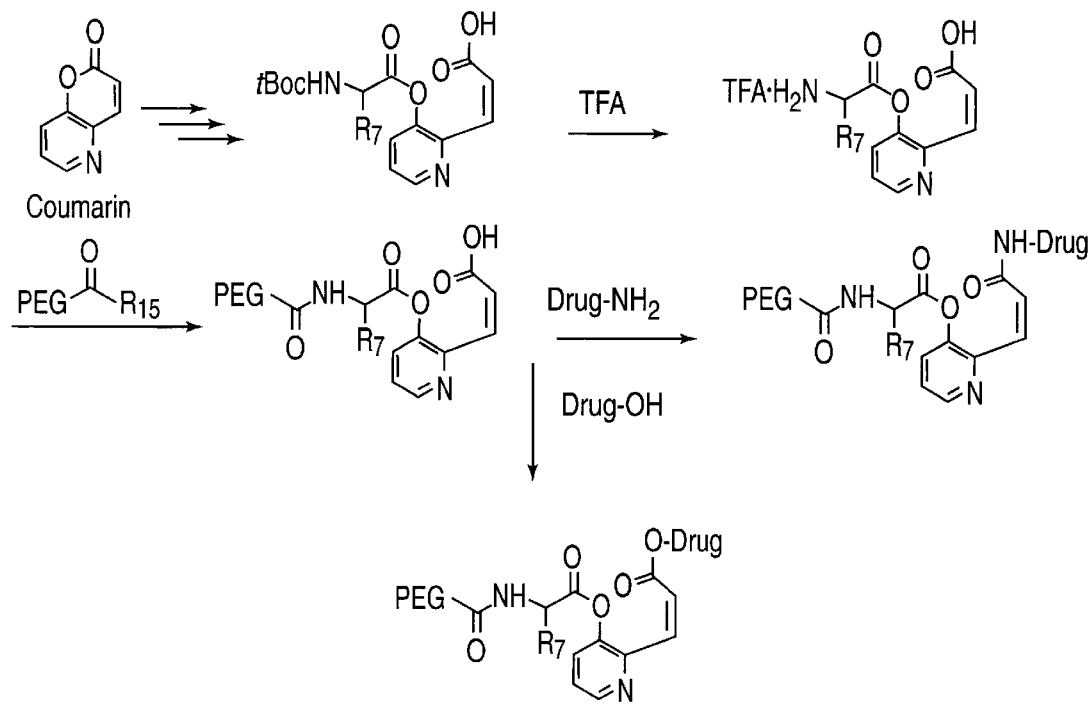

Similar techniques are employed when other aromatic moieties are used. As can be seen in FIGS. 2 and 3, the preparation of the activated polymer systems and the double prodrugs of the present invention proceed in substantially the same manner as when coumarin is used as the starting material.

Figure 4:
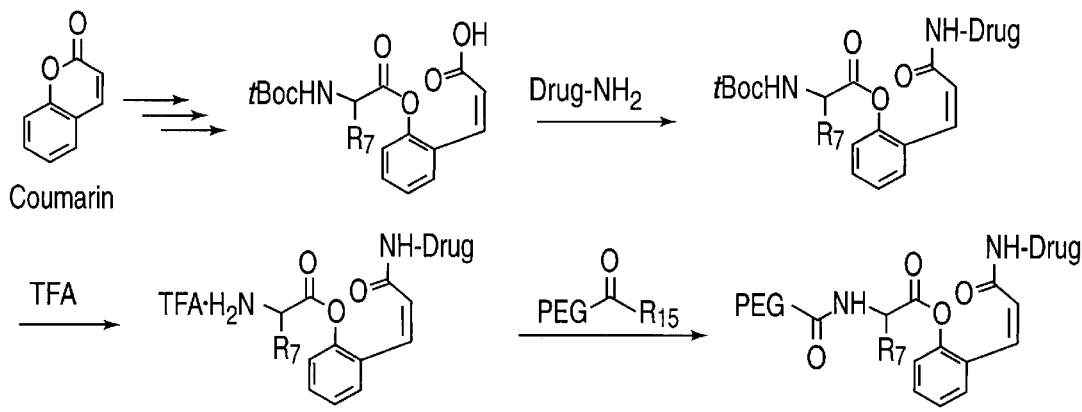
Figure 5:
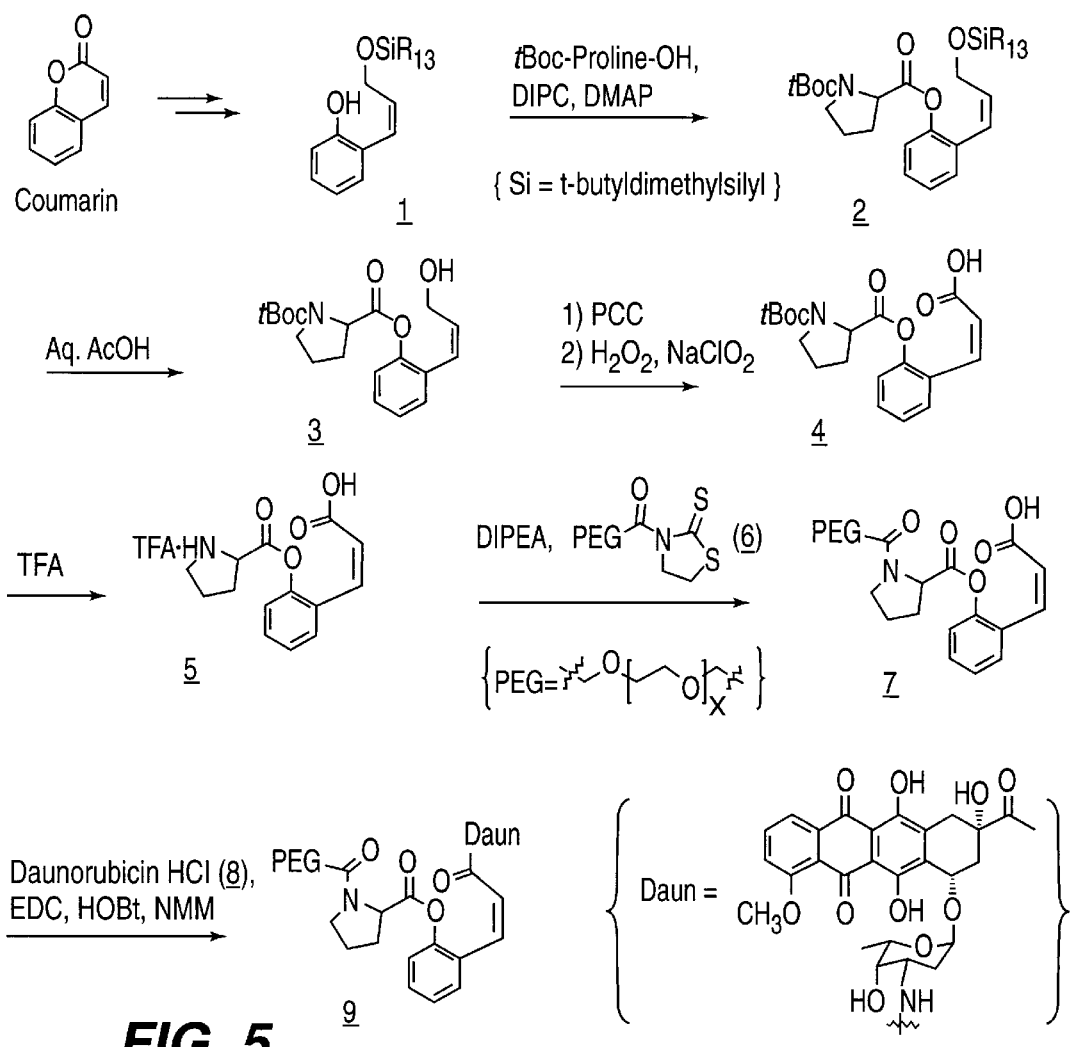
FIG. 5 illustrates reaction schemes associated with Examples 1–6.

Alternatively, as shown in FIG. 4, which also uses coumarin as the illustrative Ar moiety, the transport form (PEG-prodrug) can be prepared by:

a. attaching the parent amine-containing or hydroxyl-containing compound residue B to the intermediate compound (III);

b. removing the protecting group; and c. reacting the unprotected intermediate with an activated polymer or polymer-spacer to form the activated double prodrug.

It will be understood by the artisan that this reaction can be used to form other aromatic-based compounds when non-coumarin starting materials are employed, see, for example, the starting materials used in FIGS. 2 and 3.

Although FIG. 4 does not show the reaction scheme for an OH-containing target, the reaction would nonetheless proceed in the manner illustrated with an ester bond being formed between the drug residue and the transport system.

Intermediate compound (III) can be prepared using standard organic synthesis techniques. For example, blocked coumarin derivatives and related compounds can be synthesized using a procedure similar to or as that disclosed by Binghe Wang, et al. in *Bioorganic & Medicinal Chemistry Letters*, Vol.6, No.23, pp 2823–2826, 1996. supra, the disclosure of which is incorporated herein by reference.

Attachment of the parent amine-containing compound to intermediate compound (III) or (IV) can be carried out using standard organic synthesis techniques using coupling agents known to those of ordinary skill in the art such as 1,3-diisopropylcarbodiimide (DIPC), dialkyl carbodiimides, 2-halo-1-alkylpyridimium halides, 1-(3-dimethylaminopropyl)-3-ethyl carbodiimide (EDC), propane phosphonic acid cyclic anhydride (PPACA) and phenyl dichlorophosphates. Alternatively, when B is a good leaving group such as those listed below in F.1., a coupling agent is not required and the reaction proceeds in the presence of a base.

Generally, the double prodrugs of the invention are preferably prepared either by reacting the activated transport form described above as compound (IV) with the parent compound in the presence of a coupling agent such as DIPC, EDC, DMAP, phenyldichlorophosphate, etc. or base, if required (see FIG. 1) or attaching the parent compound to the intermediate compound (formula III) and thereafter reacting the resultant compound with an activated polymer as schematically shown in FIG. 4. In either case, the resulting conjugated double prodrug composition is then recovered or isolated using techniques known to those of ordinary skill, i.e. recrystallized then filtered.

Preferably the substituents are reacted in an inert solvent such as methylene chloride, chloroform, toluene, DMF or mixtures thereof. The reaction also preferably is conducted in the presence of a base, such as dimethylaminopyridine, diisopropylethylamine, pyridine, triethylamine, etc. to neutralize any acids generated and at a temperature from 0° C. up to about 40° C. (room temperature).

Removal of the protecting group is carried out in the same manner as described in the first method.

F. The Leaving Group or Residue Portion "B"

1. Leaving Groups

In those aspects where B is an leaving group, suitable groups include, without limitations, moieties such as N-hydroxybenzotriazolyl, halogen, N-hydroxyphthalimidyl, p-nitrophenoxy, imidazolyl, N-hydroxysuccinimidyl; thiazolidinyl thione, or other good leaving groups as will be apparent to those of ordinary skill. The leaving groups are attached to the aromatic, i.e. coumarin-or coumarin derivative portion of the compound after the "double" prodrug portion, i.e. the PEG and spacer has been attached. See, for illustrative purposes, Method A in FIG. 1. In the last step, instead of reacting the double prodrug carrier portion with a Drug-NH$_2$ or Drug-OH, it is reacted with a moiety which results in attaching the desired leaving group, i.e. PNP chloroformate or disuccinimidyl carbonate (DSC), etc. The synthesis reactions used and described herein will be understood by those of ordinary skill without undue experimentation. For purposes of illustration and not limitation, generally, the activated forms of the double prodrug transport system, i.e. when B is a leaving group not a drug residue, are prepared by acylating a compound of Formula (III) with a moiety which results in the attachment of the polymeric portion and thereafter reacting the acylated resultant compound with an activating group for coupling to a target, e.g., compounds such as 4-nitrophenylchloroformate, DSC, carbonyldiimidazole, thiazolidine thione, etc. to provide the desired "activated" derivative.

Once in place, the "activated" form of the PEG double prodrug is ready for conjugation with an amine-containing or hydroxyl-containing compound. Some preferred activated transport forms are shown below:

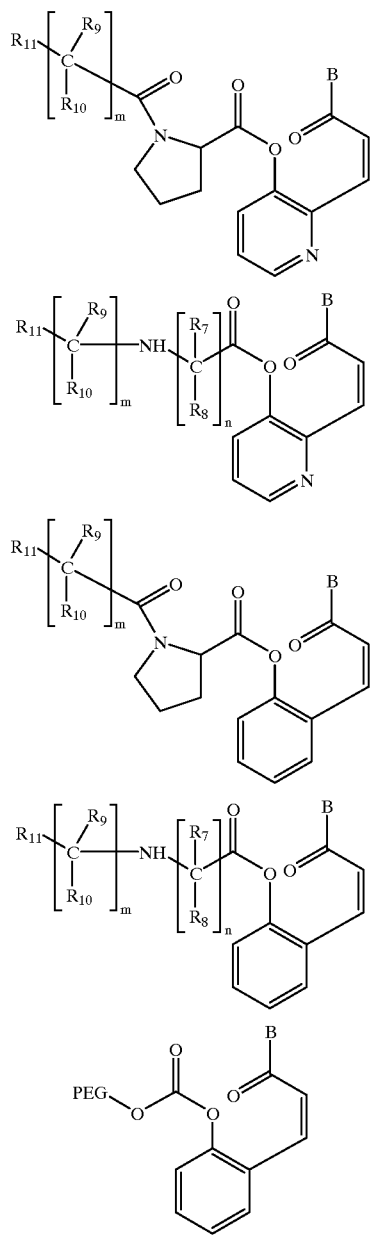

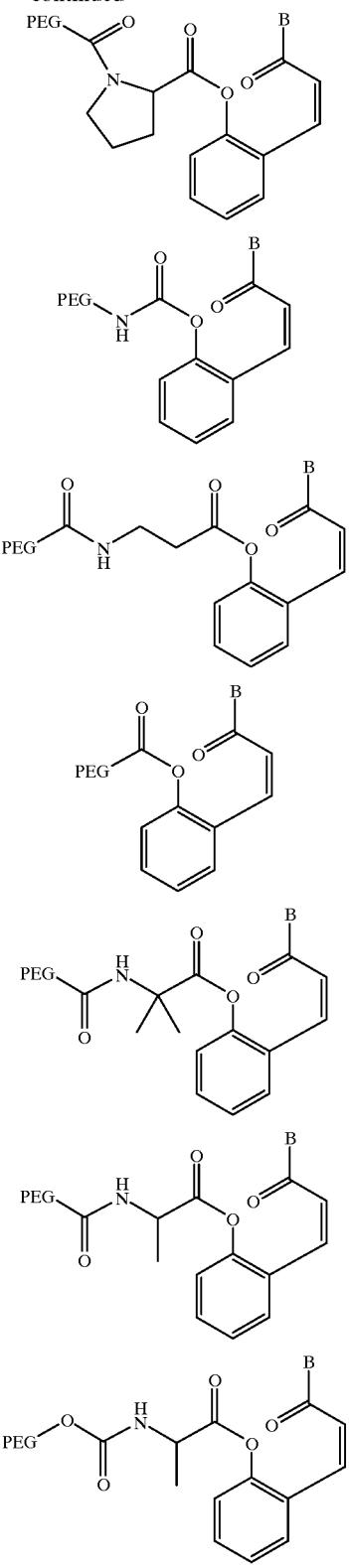

2. Residues of Amine-containing Compounds

In those aspects of the invention where B is a residue of an amine-containing compound, a non-limiting list of such suitable compounds include residues of organic compounds, enzymes, proteins, polypeptides, etc. Organic compounds include, without limitation, moieties such as anthracycline compounds including daunorubicin, doxorubicin; p-aminoaniline mustard, Ara-C (cytosine arabinoside) and related compounds, gemcitabine, etc. Alternatively, B can be a residue of an amine-containing cardiovascular agent, anti-neoplastic, anti-infective, anti-fungal such as nystatin or amphotericin B, anti-anxiety agent, gastrointestinal agent, central nervous system-activating agent, analgesic, fertility agent, contraceptive agent, anti-inflammatory agent, steroidal agent, anti-urecemic agent, vasodilating agent, vasoconstricting agent, etc.

Suitable proteins, polypeptides, enzymes, peptides and the like having at least one available amino group for polymer attachment include materials which have physiological or pharmacological activities as well as those which are able to catalyze reactions in organic solvents. The only other requirement of the amine-containing materials is that they maintain at least some portion of the activity associated with the unmodified protein, enzyme, peptide, etc. after the prodrug transport portion has hydrolyzed.

Proteins, polypeptides and peptides of interest include, but are not limited to, hemoglobin, serum proteins such as blood factors including Factors VII, VIII, and IX; immunoglobulins, cytokines such as interleukins, i.e. IL-1 through IL-13, α-, β- and γ-interferons, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors and related proteins, growth factors such as transforming growth factors, such as TGFα's or TGFβ's and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the proteins of the present invention.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Also included herein is any portion of a biological polymer demonstrating in vivo bioactivity. This includes amino acid sequences, nucleic acids (DNA, RNA), peptide nucleic acids (PNA), antibody fragments, single chain binding proteins, see, for example U.S. Pat. No. 4,946,778, disclosure of which is incorporated herein by reference, binding molecules including fusions of antibodies or fragments, polyclonal antibodies, monoclonal antibodies and catalytic antibodies.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues. Transgenic insects and baculovirus expression systems are also contemplated as sources. Moreover, mutant versions of proteins, such as mutant interferons are also within the scope of the invention.

Other proteins of interest are allergen proteins such as ragweed, Antigen E, honeybee venom, mite allergen, and the like. The foregoing is illustrative of the proteins which are suitable for the present invention. It is to be understood that those proteins, as defined herein, not specifically mentioned but having an available amino group are also intended and are within the scope of the present invention.

In a preferred aspect of the invention, the amino-containing compound is a biologically active compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds can be similarly modified without undue experimentation. It is to be understood that those biologically active materials not specifically mentioned but having suitable amino-groups are also intended and are within the scope of the present invention.

The only limitations on the types of amino-containing molecules suitable for inclusion herein is that there is available at least one (primary or secondary) amine containing position which can react and link with a carrier portion and that there is not substantial loss of bioactivity after the double prodrug system releases and regenerates the parent compound.

3. Residues of Hydroxyl-Containing Compounds a. Camptothecin and Related Topoisomerase I Inhibitors Camptothecin is a water-insoluble cytotoxic alkaloid produced by *Camptotheca accuminata* trees indigenous to China and *Nothapodytes foetida* trees indigenous to India. Camptothecin and related compounds and analogs are also known to be potential anticancer or antitumor agents and have been shown to exhibit these activities in vitro and in vivo. Camptothecin and related compounds are also candidates for conversion to the double prodrugs of the present invention. Camptothecin and certain related analogues share the structure:

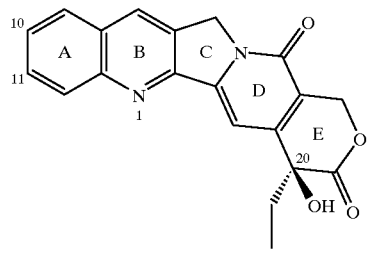

From this core structure, several known analogs have been prepared. For example, the A ring in either or both of the 10- and 11-positions can be substituted with an OH. The A ring can also be substituted in the 9-position with a straight or branched $C_{1-30}$ alkyl or $C_{1-17}$ alkoxy, optionally linked to the ring by a heteroatom i.e. —O or S. The B ring can be substituted in the 7-position with a straight or branched $C_{1-30}$ alkyl or substituted alkyl-, $C_{5-8}$ cycloakyl, $C_{1-30}$ alkoxy, phenyl alkyl, etc., alkyl carbamate, alkyl carbazides, phenyl hydrazine derivatives, amino-, aminoalkyl-, aralkyl, etc. Other substitutions are possible in the C, D and E rings. See, for example, U.S. Pat. Nos. 5,004,758; 4,943,579; Re 32,518, the contents of which are incorporated herein by reference. Such derivatives can be made using known synthetic techniques without undue experimentation. Preferred camptothecin derivatives for use herein include those which include a 20-OH or another OH moiety which is capable of reacting directly with activated forms of the polymer transport systems described herein or to the linking moiety intermediates, e.g. iminodiacetic acid, etc., which are then attached to a polymer such as PEG. Reference to camptothecin analogs herein has been made for purposes of illustration and not limitation.

b. Taxanes and Paclitaxel Derivatives

One class of compounds included in the double prodrug compositions of the present invention is taxanes. For purposes of the present invention, the term "taxane" includes all compounds within the taxane family of terpenes. Thus, taxol (paclitaxel), 3'-substituted tert-butoxy-carbonyl-amine derivatives (taxoteres) and the like as well as other analogs which are readily synthesized using standard organic techniques or are available from commercial sources such as Sigma Chemical of St. Louis, Mo. are within the scope of the present invention. Representative taxanes are shown below.

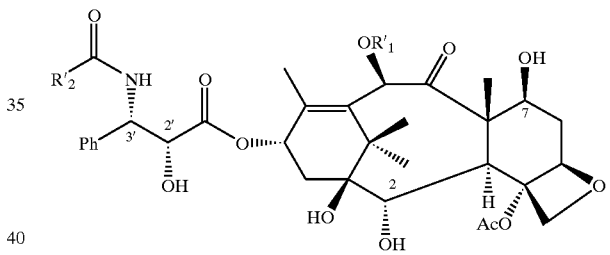

Paclitaxel: $R'_1=C_6H_5$; $R'_2=CH_3CO$; Taxotere: $R'_1=(CH_3)_3CO$; $R'_2=H$

These derivatives have been found to be effective anti-cancer agents. Numerous studies indicate that the agents have activity against several malignancies. To date, their use has been severely limited by, among other things, their short supply, poor water solubility and hypersensitivity. It is to be understood that other taxanes including the 7-aryl-carbamates and 7-carbazates disclosed in commonly assigned U.S. Pat. Nos. 5,622,986 and 5,547,981 can also be included in the double prodrugs of the present invention. The contents of the foregoing U.S. patents are incorporated herein by reference. The only limitation on the taxane is that it must be capable of undergoing a hydroxyl based substitution reaction such as at the 2' position. Paclitaxel, however, is a preferred taxane.

c. Additional Biologically-Active Moieties

In addition to the foregoing molecules, the double pro-drug formulations of the present invention can be prepared using many other compounds. For example, biologically-active compounds such as gemcitabine:

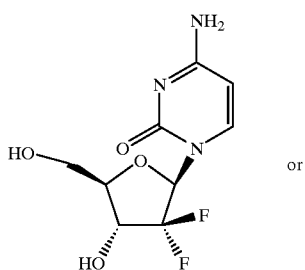

podophyllotoxin:

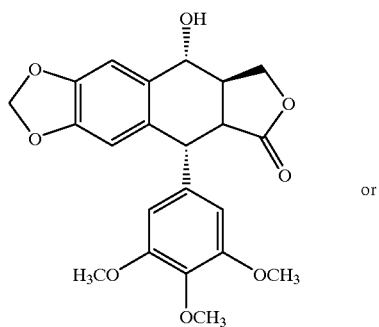

triazole-based antifungal agents such as fluconazole:

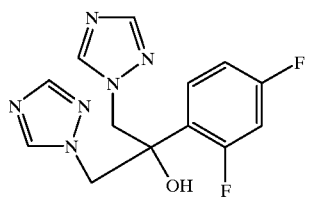

or ciclopirox:

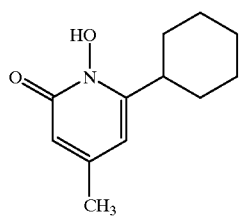

can be used.

The parent compounds selected for double prodrug forms need not be substantially water-insoluble, although the polymer-based double prodrugs of the present invention are especially well suited for delivering such water-insoluble compounds. Other useful parent compounds include, for example, certain low molecular weight biologically active proteins, enzymes and peptides, including peptido glycans, as well as other anti-tumor agents; cardiovascular agents such as forskolin; anti-neoplastics such as combretastatin, vinblastine, doxorubicin, Ara-C, maytansine, etc.; anti-infectives such as vancomycin, erythromycin, etc.; anti-fungals such as nystatin, amphoteracin B, triazoles, papulocandins, pneumocandins, echinocandins, polyoxins, nikkomycins, pradimicins, benanomicins, etc. see, "Antibiotics That Inhibit Fungal Cell Wall Development" *Annu. Rev. Microbiol.* 1994, 48:471–97, the contents of which are incorporated herein by reference; anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

It is noted that parent compounds suitable for incorporation into the double prodrug compositions of the invention, may themselves be substances/compounds which are not active after hydrolytic release from the linked composition, but which will become active after undergoing a further chemical process/reaction. For example, an anti-cancer drug that is delivered to the bloodstream by the double prodrug transport system, may remain inactive until entering a cancer or tumor cell, whereupon it is activated by the cancer or tumor cell chemistry, e.g., by an enzymatic reaction unique to that cell.

After conjugation, the remaining portion of the amine-containing or hydroxyl-containing compound is referred to as the residue of the unconjugated compound.

4. Polymeric Hybrid Transport Systems

In another aspect of the invention there are provided hybrid types of the polymeric double prodrug system described herein. In particular, the hybrid system includes not only the reversible double prodrug system but also a second polymeric system based on more permanent types of linkages. The hybrids can be prepared by at least two methods. For example, the aromatic-based double prodrug protein conjugate can be first synthesized, and then PEGylated using any art-recognized activated polymer such as thiazolidine thione or succinimidyl carbonate-activated PEG. Alternatively, the more permanent conjugation reaction can be performed first (i.e. the parent compound is PEGylated) and the resultant conjugates can be used to form the aromatic-based double prodrug conjugates described herein. It will be understood that the hybrid systems will be better suited for proteins, enzymes and the like where multiple amino groups or a combination of amino and hydroxyl groups are available for attachment of the polymeric amino prodrug. For purposes of the present invention, "activated polymers" will be understood to include polymers containing one or more terminal groups which are capable of reacting with one or more α-amino groups, ε-amino groups, histidine nitrogens, carboxyl groups, sulfhydryl groups, etc. found on enzymes, proteins, etc., as well as such groups found on synthetically prepared organic compounds.

The activating terminal moiety can be any group which facilitates conjugation of the polymers with the biologically active material, i.e. protein, enzyme, etc. either before of after the double prodrug transport system of the present invention has been synthesized. See, for example, U.S. Pat. No. 4,179,337, the disclosure of which is hereby incorporated by reference. Such activating groups can be a moiety selected from:

I. Functional groups capable of reacting with an amino group such as:
   a) carbonates such as the p-nitrophenyl, or succinimidyl; see, for example, U.S. Pat. No. 5,122,614, the disclosure of which is hereby incorporated by reference;
   b) carbonyl imidazole;
   c) azlactones; see, for example, U.S. Pat. No. 5,321,095, the disclosure of which is hereby incorporated by reference;
   d) cyclic imide thiones see, for example, U.S. Pat. No. 5,349,001, the disclosure of which is hereby incorporated by reference; or e) isocyanates or isothiocyanates.
f) active esters such as N-hydroxy-succinimidyl or N-hydroxybenzotriazolyl.

II. Functional groups capable of reacting with carboxylic acid groups and reactive carbonyl groups such as:
   a) primary amines; or
   b) hydrazine and hydrazide functional groups such as the acyl hydrazides, carbazates, semicarbazates, thiocarbazates, etc.

III. Functional groups capable of reacting with mercapto or sulfhydryl groups such as maleimides; see, for example, Shearwater Polymers Catalog "Polyethylene Glycol Derivatives 1997–1998", the disclosure of which is hereby incorporated by reference;

IV. Functional groups capable of reacting with hydroxyl groups such as (carboxylic) acids or other nucleophiles capable of reacting with an electrophilic center, such as isocyanate, activated esters or carbonates, cyclic imides, thiones, etc.

The activating moiety can also include a spacer moiety located proximal to the polymer. The spacer moiety may be a heteroalkyl, alkoxy, alkyl containing up to 18 carbon atoms or even an additional polymer chain. The spacer moieties can added using standard synthesis techniques.

G. Methods of Treatment

Another aspect of the present invention provides methods of treatment for various medical conditions in mammals. The methods include administering to the mammal in need of such treatment, an effective amount of a composition of the invention, as described herein, such as a double prodrug of doxorubicin The prodrug compositions are useful for, among other things, treating diseases which are similar to those which are treated with the parent compound, e.g. enzyme replacement therapy, neoplastic disease, reducing tumor burden, preventing metastasis of neoplasms and preventing recurrences of tumor/neoplastic growths in mammals.

The amount of the prodrug that is administered will depend upon the amount of the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, double prodrug polymeric derivatives of nitrogen mustard derivatives are administered in amounts ranging from about 5 to about 500 mg/M$^2$ per day. The range set forth above is illustrative and those skilled in the art will determine the optimal dosing of the prodrug selected based on clinical experience and the treatment indication. Actual dosages will be apparent to the artisan without undue experimentation.

The compositions, including prodrugs, of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof.

H. EXAMPLES

The following examples serve to provide further appreciation of the invention but are not meant in any way to restrict the effective scope of the invention. The underlined and bold-faced numbers recited in the Examples correspond to those shown in the Figures.

Example 1

Compound 1: t-Boc-proline ester of 1-O-t-butyldimethylsilyl-3-(2'-hydroxyphenyl)-2-propenol, 1

1,3-diisopropylcarbodiimide (392 mg, 3.11 mmol) is added to a mixture of 0.5 g (1.89 mmol) of 1-O-t-butyldimethylsilyl-3-(2'-hydroxyphenyl)-2-propenol, 1 (synthesized using the procedure of B. Wang, et al., *Bioorg. & Med. Chem. Lett.*, 1996, 6, 945.), 568 mg (4.66 mmol) of 4-dimethylaminopyridine, and 668 mg (3.11 mmol) of N-t-Boc-proline in 15 mL of anhydrous dichloromethane at 0° C. The mixture is stirred at room temperature overnight, filtered, and concentrated. The residue is purified by column chromatography on silica gel (ethyl acetate-hexane=3:7, v/v) to give 2.

Example 2

Compound 3: t-Boc-proline ester of 3-(2'-hydroxyphenyl)-2-propenol

A solution of 2.82 g (6.10 mmol) of 2 in 10 mL of tetrahydrofuran, 10 mL of water and 30 mL of glacial acetic acid is stirred at room temperature for 1 hour. The solvent is removed in vacuo to give product 3.

Example 3

Compound 4: Oxidation of t-Boc-proline ester of 3-(2'-hydroxyphenyl)-2-propenol, 3

A solution of 1.4 g (4.1 mmol) of 3 in 75 mL of anhydrous dichloromethane is added to a solution of 1.64 g (7.6 mmol) of pyridinium chlorochromate in 75 mL of anhydrous dichloromethane. The mixture is stirred at room temperature for 1 hour followed by filtration through celite. The solvent is removed in vacuo and the residue is purified by silica gel column chromatography (ethyl acetate/hexane=3:7, v/v). The product, aldehyde, is dissolved in 4.1 mL of acetonitrile, and 132 mg (1.1 mmol) of sodium phosphate in 1.65 mL of water is added to the solution. A solution of 648 mg (5.7 mmol) of 80% sodium chlorite in 5.7 mL of water is added to the mixture slowly in an ice-water bath. The mixture is stirred for 2 hours and the reaction is quenched with sodium sulfite followed by addition of 1N HCl to adjust the pH to 1–2. The mixture is extracted with ethyl acetate (75 mL). The organic layer is washed with brine (2×25 mL) and dried over anhydrous magnesium sulfate. Solvent is removed under reduced pressure to give 4.

Example 4

Compound 5: Trifluoroacetic acid salt of proline ester of 3-(2'-hydroxyphenyl)-2-propenoic acid 0.55 g (1.52 mmol) of 4 is stirred in 10 mL of trifluoroacetic acid-dichloromethane (1:1, v/v) at room temperature for 1 hour. Solvent is removed in vacuo to give 5.

Example 5

Compound 7: Coupling of 5 with PEG (40 kDa) dithiazolidine thione, 6

52.6 mg (0.41 mmol) of N,N-diisopropylethylamine is added to the solution of 65 mg (0.17 mmol) of 5 and 1 g (0.025 mmol) of PEG (40 kDa) dithiazolidine thione (6) in 15 mL of anhydrous dichloromethane. The mixture is stirred at room temperature overnight. The solvent is removed in vacuo and the residue is recrystallized from 2-propanol to give 7 as a white solid.

Example 6

Compound 9: Coupling of 7 with daunorubicin hydrochloride, 8

13.2 mg (0.07 mmol) of 1-(3-dimethylaminopropyl)-3-ethylcarbodiimide hydrochloride is added to the mixture of 0.35 g (0.01 mmol) of 7, 29 mg (0.05 mmol) of daunorubicin hydrochloride (8), 13.9 mg (0.14 mmol) of N-methylmorpholine, and 6.97 mg (0.05 mmol) of 1-hydroxybenzotriazole hydrate in 20 mL of anhydrous dichloromethane at 0 °C. The reaction mixture is stirred at room temperature overnight and filtered. The filtrate is concentrated in vacuo and the residue is recrystallized from 2-propanol (50 mL) to give 9.

Example 7

Compound 10: Coupling of 7 with N-Hydroxysuccinimide 2.5 g (0.47 mmol) of 7 and 108 mg (0.94 mmol) of N-hydroxysuccinimide are dissolved in 40 mL of anhydrous dichloromethane at 0° C. 114 mg (0.94 mmol) of DMAP and 118 mg (0.94 mmol) of DIPC are added to the mixture. The reaction mixture is stirred overnight at ambient temperature. The solvent is removed in vacuo and the residue is recrystallized from 2-propanol to give 10 as a white solid.

Example 8

Compound 12: Conjugation of 10 to (L)-Asparaginase 450 mg (0.083 mmol, 317 equiv.) of PEG linker, 10, is added to 37.5 mg (416 µL, 0.00027 mmol) of native (L)-asparaginase, 11, in 3 mL of sodium phosphate buffer (0.1 M, pH 7.8) with gentle stirring. The solution is stirred at 30° C. for 30 min. A GPC column (Zorbax GF-450) is used to monitor PEG conjugation: The PEG-Asp conjugate 12 has a retention time of about 8.5 min. At the end of the reaction (as evidenced by the absence of native enzyme), the mixture was diluted with 12 mL of formulation buffer (0.05 M sodium phosphate, 0.85% sodium chloride, pH 7.3) and diafiltered with a Centriprep concentrator (Amicon) having a molecular weight cut-off 50,000 daltons to remove the unreacted PEG. Diafiltration is continued as needed at 4° C. until no more free PEG is detected by mixing equal amount of filtrate and 0.1% PMA (polymethacrylic acid in 0.1 M HCl).

The product, 12, is not stable in basic buffer solution for prolonged periods of time, therefore the solution is lyophilized and 12 is stored in the freezer (−20 ° C.). After 15 days of storage in this manner, GPC analysis indicates less than 0.8% decomposition. The specific activity of freshly prepared 12 is found to be about 137 IU/mg (native asparaginase=217 IU/mg). Protein modification of asparaginase with SS-PEG (a permanent linker) using a procedure corresponding to that described in the aforementioned U.S. Pat. No. 4,179,337 gives a permanent bond PEG conjugate with similar activity of 120 IU/mg. A TNBS assay is used to calculate the percentage modification of the protein, and the Biuret assay is used to check the protein concentration.

Example 9

Figure 6:
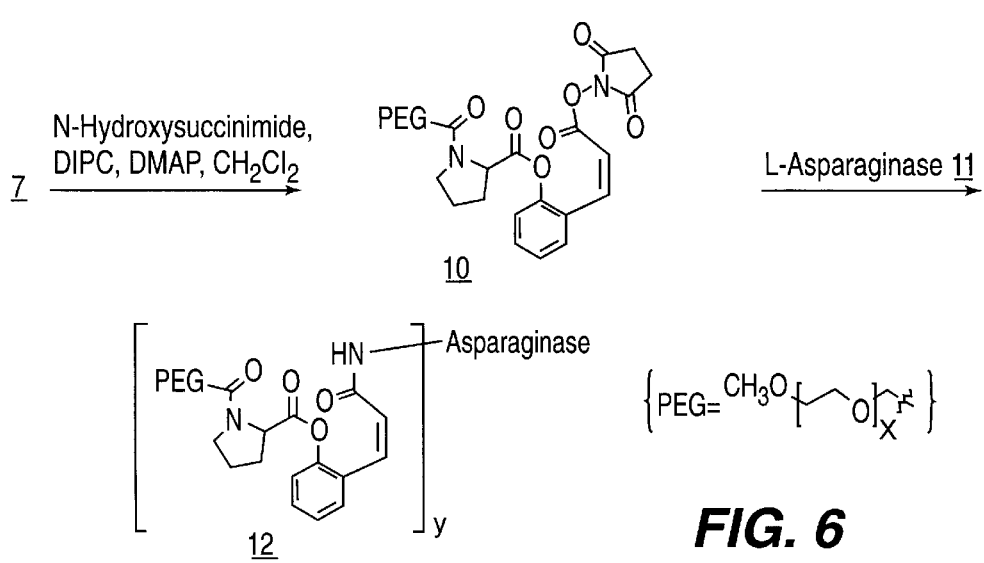
FIG. 6 illustrates a reaction scheme associated with Examples 7 and 8.

Compound 13: A Protein Hybrid—Conjugation of 12 with SS-PEG 393 mg (0.073 mmol, 70 equiv.) of 10 is reacted with 150 mg (1.664 mL, 0.00106 mmol) of native (L)-asparaginase, 11, in 30 mL of sodium phosphate buffer (0.1 M, pH 7.8) as described in Example 8 at 30° C. for 15 minutes to provide a solution of 12, where (y) represents the number of polymer strands attached to the L-asparaginase, followed by the addition of 1.272 g (0.245 mmol, 230 equiv.) of SS-PEG. The reaction solution is stirred for another 15 minutes. The pH of the reaction mixture is maintained at 7.8 with 0.5 M sodium hydroxide. The reaction mixture is diluted with 30 mL of sterile water and diafiltered using a Centriprep concentrator (Amicon) having a molecular weight cut-off of 50,000 daltons to remove any unreacted PEG. Diafiltration is continued as needed at 4° C. until no more free PEG is detected by mixing equal amount of filtrate and 0.1% PMA (polymethacrylic acid in 0.1 M HCl). A GPC column (Zorbax GF-450) is used to follow the course of the reaction. The final solution of product, 13, (not shown in FIG. 6) is lyophilized and stored in the freezer.

Example 10

Compound 14: Demonstration of Selective Removal of Reversible PEG Linker from the Hybrid, 13-Generation of a Permanently Modified Asparaginase, 14

100 mg of hybrid linker modified asparaginase, 13, is dissolved in 30 mL of pH 7.8 phosphate buffer and stirred at 30° C. overnight. This solution is diluted with 30 mL of sterile water, and diafiltered with a Centriprep concentrator (Amicon) having a molecular weight cut off of 50,000 daltons to remove the free PEG which is formed by selective cleavage of the conjugated from reversible PEG linker, 7. The solution now contains only SS-PEG conjugated asparaginase, 14. Thus the reversible linker is hydrolyzed, leaving only the relatively permanently bonded PEG attached to asparaginase.

The various publications, patents, patent applications and published applications mentioned in this application are hereby incorporated by reference herein.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

We claim:

1. A compound of the formula:

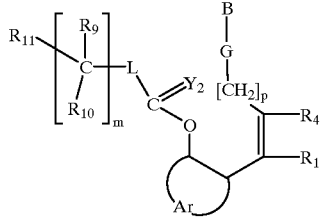
(I)

wherein

L is 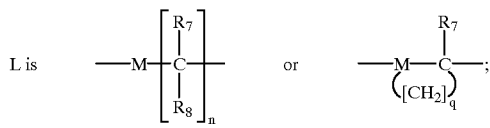

B is H, OH, OSiR$_{13}$, a residue of an amine-containing target moiety or a residue of a hydroxyl-containing target moiety;

G is

or CH$_2$;

Y$_1$ and Y$_2$ are independently O or S;

M is X or Q; where

X is an electron withdrawing group;

Q is a moiety containing a free electron pair positioned three to six atoms from C(=Y$_2$);

R$_7$, R$_8$, R$_9$, R$_{10}$ and R$_{13}$ are independently selected from the group consisting of hydrogen, C$_{1-6}$ alkyl, C$_{3-12}$ branched alkyl, C$_{3-8}$ cycloalkyl, C$_{1-6}$ substituted alkyl, C$_{3-8}$ substituted cycloalkyl, aryl, substituted aryl, aralkyl, C$_{1-6}$ heteroalkyl, substituted C$_{1-6}$ heteroalkyl, C$_{1-6}$ alkoxy, phenoxy, C$_{1-6}$ heteroalkoxy;

R$_1$ and R$_4$ are independently selected from the group consisting of hydrogen, C$_{1-6}$ alkyl, C$_{3-12}$ branched alkyl, C$_{3-8}$ cycloalkyl, C$_{1-6}$ substituted alkyl, C$_{3-8}$ substituted cycloalkyl, aryl, substituted aryl, aralkyl, C$_{1-6}$ heteroalkyl, substituted C$_{1-6}$ heteroalkyl, C$_{1-6}$ alkoxy, phenoxy, C$_{1-6}$ heteroalkoxy, cyano, nitro, carboxyl, acyl, substituted acyl, carboxyalkyl;

Ar is a moiety which when included in Formula (I) forms a multi-substituted aromatic hydrocarbon or a multi-substituted heterocyclic group;

(m) is zero or one;

(n) is zero or a positive integer;

(p) is zero or one;

(q) is three or four; and

R$_{11}$ is a polymer residue.

2. The compound of claim 1, wherein the aromatic moiety formed by Ar is selected from the group consisting of:

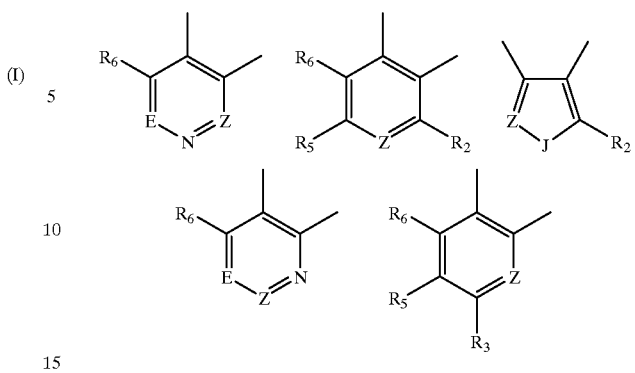

wherein J is O, S, or NR$_1$, E and Z are independently CH, O, S or NR$_1$; and R$_2$, R$_3$, R$_5$ and R$_6$ are independently selected from the group consisting of hydrogen, C$_{1-6}$ alkyl, C$_{1-6}$ alkoxy, phenoxy, C$_{1-8}$ heteroalkyl, C$_{1-8}$ heteroalkoxy, substituted C$_{1-6}$ alkyl, C$_{3-8}$ cycloalkyl, C$_{3-8}$ substituted cycloalkyl, aralkyl, aryl, and aryl substituted with moieties selected from the group consisting of halo-, nitro- and cyano-; carboxy-, carboxyalkyl, and alkyl carbonyl.

3. The compound of claim 1, wherein said substituted C$_{1-6}$ alkyl is selected from the group consisting of carboxyalkyl, aminoalkyl, dialkylaminoalkyl, hydroxyalkyl and mercaptoalkyl.

4. The compound of claim 1 wherein X is selected from the group consisting of O, NR$_{12}$,

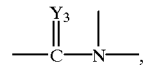

S, SO and SO$_2$, where Y$_3$ is O or S and where R$_{12}$ is selected from the group consisting of hydrogen, C$_{1-6}$ alkyl, C$_{3-12}$ branched alkyl, C$_{3-8}$ cycloalkyl, C$_{1-6}$ substituted alkyl, C$_{3-8}$ substituted cycloalkyl, aryl, substituted aryl, aralkyl, C$_{1-6}$ heteroalkyl and substituted C$_{1-6}$ heteroalkyl.

5. The compound of claim 1, wherein Q is selected from the group consisting of C$_{2-4}$ alkyl, cycloalkyl, aryl, aralkyl groups substituted with a member of the group consisting of NH, O, S, —CH$_2$—C(O)—NH—, and ortho-substituted phenyl.

6. The compound of claim 1, wherein R$_{11}$ is selected from the group consisting of —C(=Y)—(CH$_2$)$_n$—O—(CH$_2$CH$_2$O)$_x$—A, —C(=Y)—Y—(CH$_2$)$_n$—O—(CH$_2$CH$_2$O)$_x$—A and —C(=Y)—NR$_{12}$—(CH$_2$)$_n$—O—(CH$_2$CH$_2$O)$_x$—A, where R$_1$ and R$_4$ are independently selected from the group consisting of hydrogen, C$_{1-6}$ alkyl, C$_{1-6}$ heteroalkyl, substituted C$_{1-6}$ heteroalkyl and substituted C$_{1-6}$ alkyl;

(n) is zero or a positive integer;

Y is O or S;

A is a capping group; and (x) represents the degree of polymerization.

7. A method for preparing a polymeric prodrug comprising:

a. contacting an intermediate compound (III)

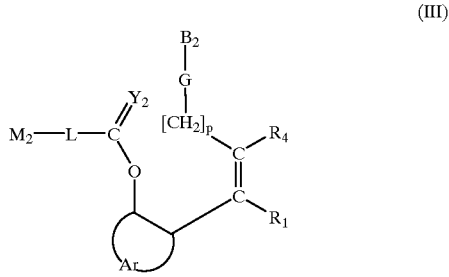

where $M_2$ is a cleavable or reversible protecting group;

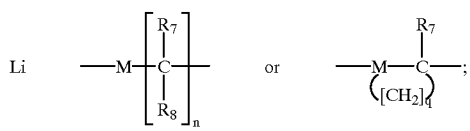

$B_2$ is a leaving group;
G is

or $CH_2$;

$Y_1$ and $Y_2$ are independently O or S;

M is X or Q; where

X is an electron withdrawing group;

Q is a moiety containing a free electron pair positioned three to six atoms from $C(=Y_2)$;

$R_1$ and $R_4$ are independently selected from the group consisting of hydrogen, $C_{1-6}$ alkyl, $C_{3-12}$ branched alkyl, $C_{3-8}$ cycloalkyl, $C_{1-6}$ substituted alkyl, $C_{3-8}$ substituted cycloalkyl, aryl, substituted aryl, aralkyl, $C_{1-6}$ heteroalkyl, substituted $C_{1-6}$ heteroalkyl, $C_{1-6}$ alkoxy, phenoxy, $C_{1-6}$ heteroalkoxy, cyano, nitro, carboxyl, acyl, substituted acyl, carboxyalkyl;

$R_7$ and $R_8$ are independently selected from the group consisting of hydrogen, $C_{1-6}$ alkyl, $C_{3-2}$ branched alkyl, $C_{3-8}$ cycloalkyl, $C_{1-6}$ substituted alkyl, $C_{3-8}$ substituted cycloalkyl, aryl substituted aryl, aralkyl, $C_{1-6}$ heteroalkyl and substituted $C_{1-6}$ heteroalkyl;

Ar is a moiety which when included in Formula (III) forms a multi-substituted aromatic hydrocarbon or a multi-substituted heterocyclic group;

(n) is zero or a positive integer;

(p) is zero, one or two;

(q) is three or four;

with an acid to deprotect the intermediate compound (III); and b. reacting the unprotected intermediate with an activated polymer.

8. A method for preparing a polymeric prodrug comprising:

a. providing an intermediate compound (III)

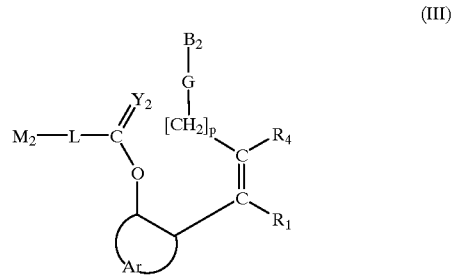

where $M_2$ is a cleavable or reversible protecting group;

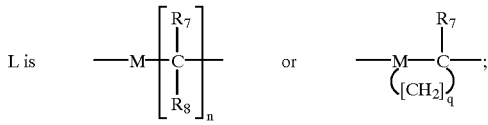

$B_2$ is a leaving group;
G is

or $CH_2$;

$Y_1$ and $Y_2$ are independently O or S;

M is X or Q; where

X is an electron withdrawing group;

Q is a moiety containing a free electron pair positioned three to six atoms from $C(=Y_2)$;

$R_1$ and $R_4$ are independently selected from the group consisting of hydrogen, $C_{1-6}$ alkyl, $C_{3-12}$ branched alkyl, $C_{3-8}$ cycloalkyl, $C_{1-6}$ substituted alkyl, $C_{3-8}$ substituted cycloalkyl, aryl, substituted aryl, aralkyl, $C_{1-6}$ heteroalkyl, substituted $C_{1-6}$ heteroalkyl, $C_{1-6}$ alkoxy, phenoxy, $C_{1-6}$ heteroalkoxy, cyano, nitro, carboxyl, acyl, substituted acyl, carboxyalkyl;

$R_7$, and $R_8$ are independently selected from the group consisting of hydrogen, $C_{1-6}$ alkyl, $C_{3-12}$ branched alkyl, $C_{3-8}$ cycloalkyl, $C_{1-6}$ substituted alkyl, $C_{3-8}$ substituted cycloalkyl, aryl, substituted aryl, aralkyl, $C_{1-6}$ heteroalkyl and substituted $C_{1-6}$ heteroalkyl;

Ar is a moiety which when included in Formula (I) forms a multi-substituted aromatic hydrocarbon or a multi-substituted heterocyclic group;

(n) is zero or a positive integer;

(p) is zero, one or two;

(q) is 3 or 4 and b. coupling the intermediate compound (III) to an amine-containing compound or a hydroxyl-containing compound to form a second intermediate;

c. deprotecting the second intermediate with an acid; and d. reacting the unprotected second intermediate with an activated polymer.

9. The compound of claim 2, wherein the aromatic moiety formed by Ar is

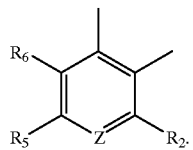

10. The compound of claim 2, wherein the aromatic moiety formed by Ar is

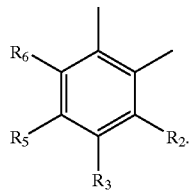

11. The compound of claim 10, wherein $R_2$ and $R_5$ are $C_{1-6}$ alkyls.

12. The compound of claim 10, wherein $R_2$ and $R_5$ are methyl.

13. The compound of claim 10, wherein $R_3$ and $R_6$ are hydrogen.

14. The compound of claim 1, wherein $R_{11}$ further comprises a capping group A.

15. The compound of claim 14, wherein A is selected from the group consisting of hydrogen, $CO_2H$, $C_{1-6}$ alkyl moiety, dialkyl acyl urea alkyl and

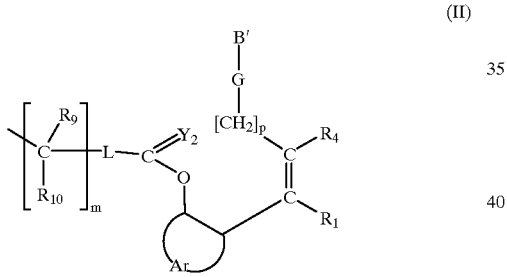

(II)

wherein B' is the same as B or another member of the group defined as B.

16. The compound of claim 1, wherein $R_1$ and $R_4$ are independently selected from the group consisting of hydrogen, $CH_3$ and $CH_2CH_3$.

17. The compound of claim 4, wherein X is selected from the group consisting

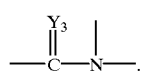

18. The compound of claim 1, wherein (n) is an integer from about 1 to about 12.

19. The compound of claim 18, wherein (n) is 1 or 2.

20. The compound of claim 1, wherein (m) is 0.

21. The compound of claim 1, wherein (p) is one.

22. The compound of claim 1, wherein (q) is 3.

23. The compound of claim 1, wherein $Y_2$ are O.

24. The compound of claim 1, wherein $R_{11}$ comprises a polyalkylene oxide.

25. The compound of claim 24, wherein said polyalkylene oxide comprises polyethylene glycol.

26. The compound of claim 1, wherein said polymer has a molecular weight of from about 2,000 to about 100,000.

27. The compound of claim 26, wherein said polymer has a molecular weight of from about 5,000 to about 40,000.

28. The compound of claim 1, wherein B is a leaving group selected from the group consisting of N-hydroxybenzotriazolyl, halogen, N-hydroxyphthalimidyl, p-nitrophenoxy, imidazolyl, N-hydroxysuccinimidyl, thiazolidinyl thione or an acid activating group.

29. The compound of claim 1, wherein B is a residue of a member of the group consisting of anthracyclines, daunorubicin, doxorubicin, p-hydroxyaniline mustard, Ara-C, and gemcitabine.

30. The compound of claim 1, wherein B is a residue of an enzyme, protein, peptide or an amine-containing compound.

31. The compound of claim 1, wherein B includes a second polymeric transport system.

32. A compound of claim 1, selected from the group consisting of:

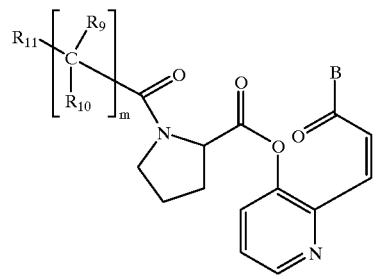

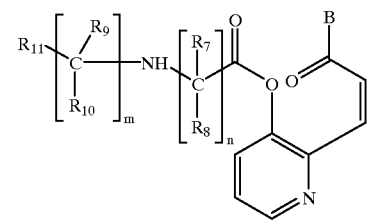

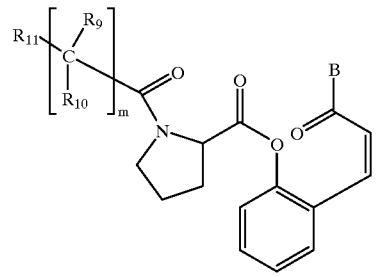

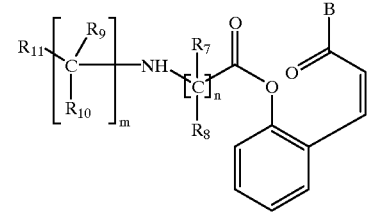

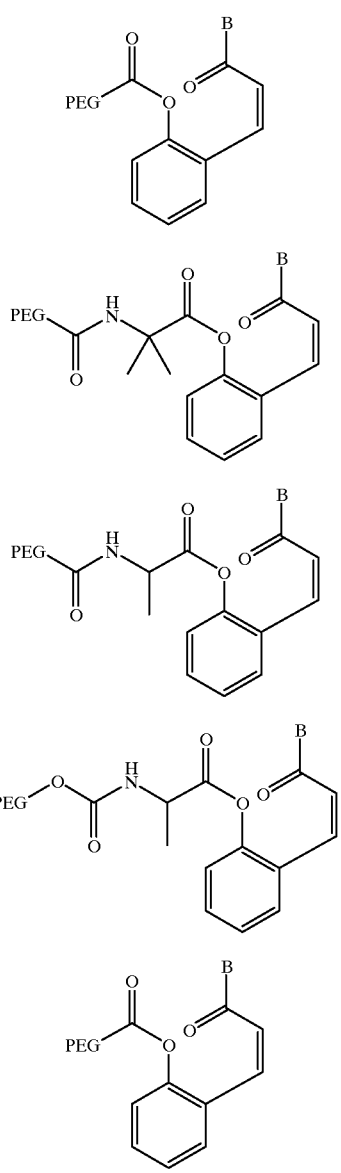

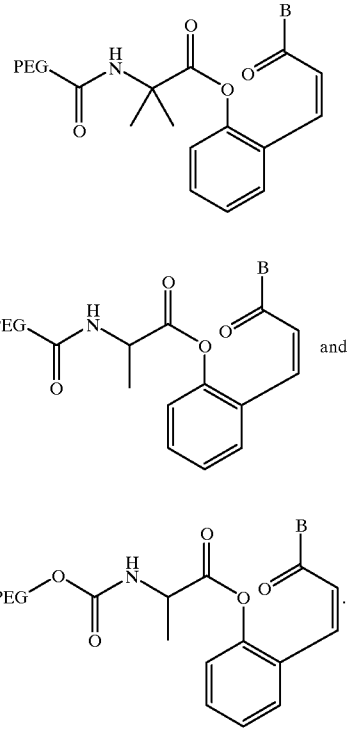

33. The method of claim 7, further comprising the step of c. reacting the resultant compound of step b with an amine-containing or hydroxyl-containing compound to form a conjugate.

34. The method of claim 33, further comprising reacting said conjugate with an activated polymer to from a polymeric hybrid transport system.

35. A method of treatment, comprising:

administering to a mammal in need of such treatment an effective amount of a compound of claim 1, wherein B is a residue of an amine-containing or hydroxyl-containing target moiety.

* * * * *

UNITED STATES PATENT AND TRADEMARK OFFICE
CERTIFICATE OF CORRECTION

PATENT NO. : 6,214,330 B1
DATED : April 10, 2001
INVENTOR(S) : Greenwald, Richard B., et al.

It is certified that error appears in the above-identified patent and that said Letters Patent is hereby corrected as shown below:

Title page,
Item [75], lines 1-2, delete "Yun H. Choc" insert -- Yun H. Choe --.

Claim 7,
Line 22, delete "Li", insert -- L is --;

Claim 17,
Line 2, after "consisting", insert -- of O, $NR_{12}$, and --;

Claim 23,
Line 1, after "wherein", insert -- $Y_1$ and --.

Signed and Sealed this

Sixteenth Day of April, 2002

Attest:

Attesting Officer

JAMES E. ROGAN
*Director of the United States Patent and Trademark Office*